US011723681B2

(12) United States Patent
Germain et al.

(10) Patent No.: US 11,723,681 B2
(45) Date of Patent: Aug. 15, 2023

(54) ARTHROSCOPIC DEVICES AND METHODS

(71) Applicant: RELIGN Corporation, Cupertino, CA (US)

(72) Inventors: Aaron Germain, San Jose, CA (US); Jacob Tonkel, San Jose, CA (US); Jan Echeverry, San Jose, CA (US)

(73) Assignee: Relign Corporation, Campbell, CA (US)

( * ) Notice: Subject to any disclaimer, the term of this patent is extended or adjusted under 35 U.S.C. 154(b) by 1079 days.

(21) Appl. No.: 16/229,538

(22) Filed: Dec. 21, 2018

(65) Prior Publication Data

US 2019/0192180 A1 Jun. 27, 2019

Related U.S. Application Data

(60) Provisional application No. 62/610,872, filed on Dec. 27, 2017.

(51) Int. Cl.
*A61B 18/14* (2006.01)
*A61B 17/32* (2006.01)
(Continued)

(52) U.S. Cl.
CPC .......... *A61B 17/32002* (2013.01); *A61B 17/320758* (2013.01); *A61B 18/148* (2013.01); *A61B 18/1482* (2013.01); *A61B 17/320783* (2013.01); *A61B 2017/0088* (2013.01); *A61B 2017/320004* (2013.01); *A61B 2017/320028* (2013.01); *A61B 2017/320032* (2013.01);
(Continued)

(58) Field of Classification Search
CPC ...... A61B 17/32002; A61B 17/320783; A61B 17/320032; A61B 2018/00208; A61B 2018/00577; A61B 2018/00589; A61B 2218/007; A61B 2017/320032
See application file for complete search history.

(56) References Cited

U.S. PATENT DOCUMENTS 5,364,395 A 11/1994 West, Jr.
6,413,256 B1 7/2002 Truckai et al.
(Continued)

FOREIGN PATENT DOCUMENTS

WO WO-2016171963 A1 10/2016
WO WO-2019133542 A1 7/2019

OTHER PUBLICATIONS

"International Application Serial No. PCT/US2018/067359, International Preliminary Report on Patentability dated Jul. 9, 2020", 9 pgs.
(Continued)

*Primary Examiner* — Jaymi E Della
(74) *Attorney, Agent, or Firm* — Schwegman Lundberg & Woessner, P.A.

(57) ABSTRACT

A tissue treatment device has a shaft assembly including an outer sleeve and an inner sleeve. The inner sleeve is co-axially and rotatably received in an axial passageway in the outer sleeve. A dielectric housing has an outer cutting window forming a distal portion of the outer sleeve, and a distal portion of the inner sleeve forms an RF electrode and has an inner cutting window formed therein. The outer and inner cutting windows have outer and inner cutting edges disposed to close together as the inner sleeve is rotated relative to the outer sleeve.

14 Claims, 15 Drawing Sheets

(51) Int. Cl.
*A61B 17/3207* (2006.01)
*A61B 18/00* (2006.01)
*A61B 17/00* (2006.01)

(52) U.S. Cl.
CPC .............. *A61B 2018/00083* (2013.01); *A61B 2018/00208* (2013.01); *A61B 2018/00577* (2013.01); *A61B 2018/00589* (2013.01); *A61B 2218/002* (2013.01); *A61B 2218/007* (2013.01)

(56) References Cited

U.S. PATENT DOCUMENTS

| | | | | |
|---|---|---|---|---|
| 6,610,059 | B1* | 8/2003 | West, Jr. | A61B 17/32002 606/41 |
| 6,821,275 | B2 | 11/2004 | Truckai et al. | |
| 6,890,332 | B2 | 5/2005 | Truckai et al. | |
| 7,150,747 | B1* | 12/2006 | McDonald | A61B 18/148 606/49 |
| 7,220,261 | B2 | 5/2007 | Truckai et al. | |
| 7,699,846 | B2 | 4/2010 | Ryan | |
| 7,744,595 | B2 | 6/2010 | Truckai et al. | |
| 8,221,404 | B2 | 7/2012 | Truckai | |
| 8,323,280 | B2 | 12/2012 | Germain et al. | |
| 8,333,763 | B2 | 12/2012 | Truckai et al. | |
| 8,702,702 | B1* | 4/2014 | Edwards | A61B 17/32002 606/50 |
| 9,204,918 | B2 | 12/2015 | Germain et al. | |
| 9,247,983 | B2 | 2/2016 | Truckai et al. | |
| 9,277,954 | B2 | 3/2016 | Germain et al. | |
| 9,549,754 | B2 | 1/2017 | Shadduck et al. | |
| 9,585,675 | B1 | 3/2017 | Germain et al. | |
| 9,592,085 | B2 | 3/2017 | Germain et al. | |
| 9,603,656 | B1 | 3/2017 | Germain et al. | |
| 9,795,434 | B2 | 10/2017 | Germain et al. | |
| 9,855,675 | B1 | 1/2018 | Germain et al. | |
| 10,022,140 | B2 | 7/2018 | Germain et al. | |
| 10,028,767 | B2 | 7/2018 | Germain et al. | |
| 10,052,149 | B2 | 8/2018 | Germain et al. | |
| 10,595,889 | B2 | 3/2020 | Germain et al. | |
| 2013/0331833 | A1* | 12/2013 | Bloom | A61B 18/1445 606/45 |
| 2015/0265337 | A1* | 9/2015 | Bloom | A61B 18/148 606/48 |
| 2016/0346036 | A1* | 12/2016 | Orczy-Timko | A61B 18/1206 |
| 2017/0202612 | A1 | 7/2017 | Germain et al. | |
| 2017/0224368 | A1* | 8/2017 | Germain | A61B 17/32002 |
| 2017/0258519 | A1 | 9/2017 | Germain et al. | |

OTHER PUBLICATIONS

Allen-Bradley. AC Braking Basics. Rockwell Automation. Feb. 2001. 4 pages. URL: http://literature.rockwellautomation.com/idc/groups/literature/documents/wp/drives-wp004_-en-p.pdf.

Allen-Bradley. What Is Regeneration? Braking / Regeneration Manual: Regeneration Overview. Revision 1.0. Rockwell Automation. Accessed Apr. 24, 2017. 6 pages. URL: https://www.ab.com/support/abdrives/documentation/techpapers/RegenOverview01.pdf.

Cales, et al. Dielectric properties of ionic conductors: Yttria stabilized zirconia and forsterite. Journal de Physique Archives, vol. 41, 1980.

International search report with written opinion dated Mar. 25, 2019 for PCT/US2018/067359.

* cited by examiner

ARTHROSCOPIC DEVICES AND METHODS

CROSS-REFERENCE TO RELATED APPLICATION

This application claims the benefit of provisional application 62/610,872, filed on Dec. 27, 2018, the full disclosure of which is incorporated herein by reference.

BACKGROUND OF THE INVENTION

1. Field of the Invention

This invention relates to a medical system that includes variations of motor-driven tubular cutter or arthroscopic shavers that are configured for both mechanical cutting and electrosurgical cutting, ablation and coagulation procedures In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, endoscopic tool systems include a reusable handpiece and a selection of interchangeable tool probes having different working ends have been proposed. Such working ends may each have two or more functionalities, such as soft tissue removal and hard tissue resection, so such tools systems can provide dozens of specific functionalities, providing great flexibility.

While a significant advantage, the need for one tool system to accommodate such flexibility is a challenge. In particular, it is necessary that the handpiece and control unit for the system be provided with correct information on the identity of the tool probe that has been attached as well as the operational parameters of the tool probe during use.

It is therefore an object of the present invention to provide improved tissue treatment devices, systems, and methods for their use, such as improved arthroscopic tissue resection devices and systems wherein a motor-driven electrosurgical device is configured for cutting and removing both bone or soft tissue from a joint or other site. It is a further object invention to provide improved systems and methods for device identification, monitoring, and control, such as controlled operational stopping and starting of motor-driven components in default positions. At least some of these objectives will be met by the inventions described herein.

2. Description of the Background Art

Commonly owned U.S. patents having relevant disclosures include U.S. Pat. Nos. 6,413,256; 6,821,275; 6,890,332; 7,220,261; 7,744,595; 8,221,404; 8,323,280; 8,333,763; 9,204,918; 9,247,983; 9,277,954; 9,585,675; 9,592,085; 9,603,656; 9,855,675; 9,795,434; 2017 10,022,140; 10,028,767; and 10,052,149.

SUMMARY OF THE INVENTION

The present invention provides multi-functional tissue treatment devices capable of performing two, three, four, or more different treatment modalities without the need to exchange devices, device components, or to reconfigure the devices in any significant manner. The tissue treatment devices of present invention may be combined with radio frequency (RF) or other electrosurgical sources as well as with electric motor drives and controllers so that the tissue treatment devices can perform a variety of tissue cutting, resecting, coagulation, and other mechanical and electrosurgical procedures by selectively driving and powering the device components and delivering RF for other electrical energy to electrodes and other energy delivery components of the devices. In this way, the number of individual devices needed to perform a surgical intervention can be reduced.

In a first aspect of the present invention, a tissue treatment device, such as an arthroscopic, laparoscopic, or other surgical tool, comprises a shaft assembly which includes an outer sleeve and an inner sleeve co-axially and rotatably received in an axial passage way of the outer sleeve. A dielectric housing has an outer cutting window which forms a distal portion of the outer sleeve, typically being a ceramic shell or enclosure having a hollow interior with a window in a wall of the housing. The ceramic housing may be attached to a metal or tube which forms a proximate portion of the outer sleeve. A distal portion of the inner sleeve forms an RF electrode and includes an inner cutting window formed therein, typically formed through a cylindrical wall of the distal region of the inner sleeve. Typically, but not necessarily, the inner sleeve may be formed from a metal or other electrically conductive material thus forming the electrode. The inner and outer cutting windows have inner and outer cutting edges which are disposed to close together, typically to pass each other in a shearing motion, as the inner sleeve is rotated relative to the outer sleeve.

The outer and inner cutting windows will be axially positioned so that they will radially align with one another as the inner sleeve is rotated relative to the outer sleeve. Thus, the inner sleeve may be rotated to a window-open position where the inner window and the outer window are aligned so that tissue may pass or be drawn into the opening formed as the windows are aligned. As the inner sleeve is further rotated about its axis, the inner cutting window will pass out of alignment with the outer cutting window until the inner and outer sleeves reach a window-closed configuration where a wall portion of the outer sleeve covers the inner cutting window and the inner sleeve. When the inner sleeve is in such window-closed configuration, a closed lower portion of the inner sleeve will be positioned within the outer cutting window and will be exposed for use as an electrode for electrosurgical coagulation or other purposes as explained more fully below.

The dialectic material of the dialectic housing typically comprises at least one of a ceramic, a glass, a polymer, or the like. In particular instances, the dialectic comprises a ceramic selected from the group consisting of alumina, zirconia, silicon nitride, yttria-stabilized zirconia, magnesia-stabilized zirconia, ceria-stabilized zirconia and zirconia toughened alumina.

Tissue treatment devices according to the present invention may be formed into systems which further comprise a motor (optionally in a removable handle) configured to selectively rotate the inner sleeve in the first and second rotational directions as well as a RF source configured to couple to the RF electrode. Such systems may further comprise a controller (optionally combined with the RF source in a control box) operably coupled to the motor and to the RF source. Using the motor, RF source, and controller, the inner sleeve can be rotated to at least its window-closed position wherein the inner window is covered by a wall of the dialectic housing and then to its window-open position when the inner window is aligned with the outer window in the dialectic housing. By continuously rotating the inner shaft relative to the outer sleeve, tissue drawn in through the aligned inner and outer cutting windows may be sheared and drawn into an interior passageway of the inner sleeve where it can optionally be withdrawn by a negative pressure applied to a proximal location along the passageway. In such instances, the controller will typically be configured to stop the motor to position the inner sleeve in at least one of the window-open and the window-closed position.

In specific instances, the controller will be configured to selectively operate the motor and the RF source in at least one of a first mode, a second mode, a third mode, and a fourth mode. In the first mode, the controller operates the motor to rotate or oscillate the inner sleeve without energizing the RF source in order to mechanically cut tissue without RF or other electrosurgical enhancement. In the second mode, the controller operates the motor to rotate or oscillate the inner sleeve and further energizes the RF source for cutting tissue with electrosurgical enhancement. In the third mode, the controller energizes the RF source while the inner sleeve remains stationary in the window-closed position. In this way, the treatment device can be used to apply a coagulative or a blade of energy to tissue through the RF electrode. In the fourth mode, the controller energizes the RF source while the inner sleeve is stationary in the window-open position to apply a coagulative or a blade of energy to tissue.

In a second aspect of the present invention, a tissue resecting system comprises a shaft assembly including an elongated outer sleeve with a distal ceramic portion having a resecting window that opens to a bore or passageway therein. An inner sleeve with a distal portion having an inner resecting window and being adapted to rotate in the bore through window-open and window-closed positions is able to thereby resect tissue and engaged by the resecting windows. The distal portion of the inner sleeve is at least partially electrically conductive to form an RF electrode.

Such tissue resecting systems may further comprise a motor configured to rotatably drive the inner sleeve relative to the outer sleeve. The system may still further comprise an RF source connected to the RF electrode. In still further embodiments, a negative pressure source may be provided and adapted to connect to a proximal end of the bore in order to draw a resected tissue through the shaft and away from the treatment region. Controllers may be provided to control the operating parameters of the motor, the RF source, and the negative pressure source. Typically, the systems further comprise a hub attached to a proximal end of the shaft assembly, where the hub is configured for detachably coupling to a handle which carries the drive motor. The inner sleeve may optionally have an opening in the surface opposed to the inner resecting window in order to allow fluid flow air through during these periods.

In a third aspect of the present invention, a method for treating tissue in a patient comprises engaging a distal end of the shaft of a tissue treatment device against a target tissue. The tissue treatment device is connected to a drive motor, and the target tissue is typically submerged in an electrically conductive fluid. The method comprises performing at least two of the following three tissue treatment operations. The first treatment operation comprises operating the drive motor to rotator oscillate an inner sleeve of the shaft without energizing the RF source to rotate an inner cutting window on the inner sleeve to mechanically cut tissue at the target tissue. The second treatment operation comprises operating the driving motor to rotate or oscillate the inner sleeve to in turn rotate or oscillate the inner cutting window on the inner sleeve and energizing the RF source to deliver a cutting current for electrosurgically cutting tissue at the targettissue. The third treatment operation comprises energizing the RF source to deliver a coagulation current to target tissue through a RF electrode on the inner sleeve while the inner sleeve is stationary.

In specific aspects, the methods of the present invention may further comprise sequentially performing all three of the three treatment operations. Further, the inner sleeve of the shaft may be rotated or oscillated relative to an outer shaft having an outer cutting window so that the inner and outer cutting windows rotate or oscillate past each other to mechanically shear tissue extending through the windows when the windows are aligned without energizing the RF source. Still further, the inner sleeve of the shaft may be rotated or oscillated relative to an outer shaft having an outer cutting window so that the inner and outer cutting windows rotate or oscillate past each other to electrosurgically cut tissue extending through the windows when the windows are aligned while energizing the RF source to apply a cutting current. Still further, the methods may comprise actuating a negative pressure source in communication with a passageway in the inner sleeve to aspirate conductive fluid and tissue to breath from the target sight as well as growing tissue through the aligned cutting windows to enhance tissue cutting, both mechanical and electrosurgical.

In other specific aspects, the present invention may be defined in the following numbered clauses:

Clause 1. A tissue resecting device for use in a conductive fluid, comprising:
  a tubular cutter comprising an outer sleeve and a co-axial inner sleeve, wherein a distal end of the outer sleeve comprises a dielectric housing with an outer resecting window therein and a distal end of the inner sleeve comprises and RF electrode with an inner resecting window therein;
  a motor configured to rotatably drive the inner sleeve relative to the outer sleeve through window-open and window-closed positions to thereby resect tissue engaged by the resecting windows; and
  an RF source operatively coupled to the RF electrode;
  wherein the outwardly exposed RF electrode surface in the window-closed is adapted to cooperate with the RF source to allow ignition of a plasma about said RF electrode surface when submerged in conductive fluid.
  wherein the inner sleeve in the window-closed position defines an outwardly exposed RF electrode surface area adapted to cooperate with the RF source to allow ignition of a plasma about said RF electrode surface area when submerged in conductive fluid.

Clause 2. The tissue resecting device of clause 1 wherein said RF electrode surface has an area of less than 15 mm$^2$, less than 10 mm$^2$ or less than 8 mm$^2$.

Clause 3. The tissue resecting device of clause 1 wherein said RF electrode surface has an area of less than 15 mm$^2$ and the RF source provides an average power of at least 100 W×

Clause 4. The tissue resecting device of clause 1 further comprising a negative pressure source coupled to a passageway in the inner sleeve communicating with the inner resecting window.

Clause 5. The tissue resecting device of clause 1 further comprising a controller configured to control operating parameters of the motor, the RF source and the negative pressure source.

Clause 6. The tissue treatment device of clause 5 wherein the controller includes an algorithm for stopping rotation of the inner sleeve in the window-closed position.

Clause 7. The tissue treatment device of clause 5 wherein the controller includes an algorithm for a second mode of operation in which the motor rotates or oscillates the inner sleeve with the RF electrode energized for electrosurgically cutting tissue.

Clause 8. The tissue treatment device of clause 5 wherein the controller includes an algorithm for a third mode of operation in which the inner sleeve is stationary and the RF electrode is energized for applying coagulative or ablative energy to tissue.

Clause 9. A tissue treatment device, comprising:
a shaft assembly having an outer sleeve and a moveable co-axial inner sleeve, wherein the outer sleeve has a cutting window therein that cooperates with shearing edges of the inner sleeve;
wherein the distal portion of the outer sleeve that carries the cutting window comprises a dielectric housing; and
wherein the distal portion of the inner sleeve that carries the shearing edges comprises an RF electrode.

Clause 10. The tissue treatment device of clause 9 wherein inner sleeve is coupled to a motor drive.

Clause 11. The tissue treatment device of clause 9 wherein the motor drive is adapted to rotates the inner sleeve.

Clause 12. The tissue treatment device of clause 9 wherein the motor drive is adapted to reciprocate the inner sleeve.

Clause 13. The tissue treatment device of clause 9 wherein the motor drive is adapted to rotate and reciprocate the inner sleeve.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
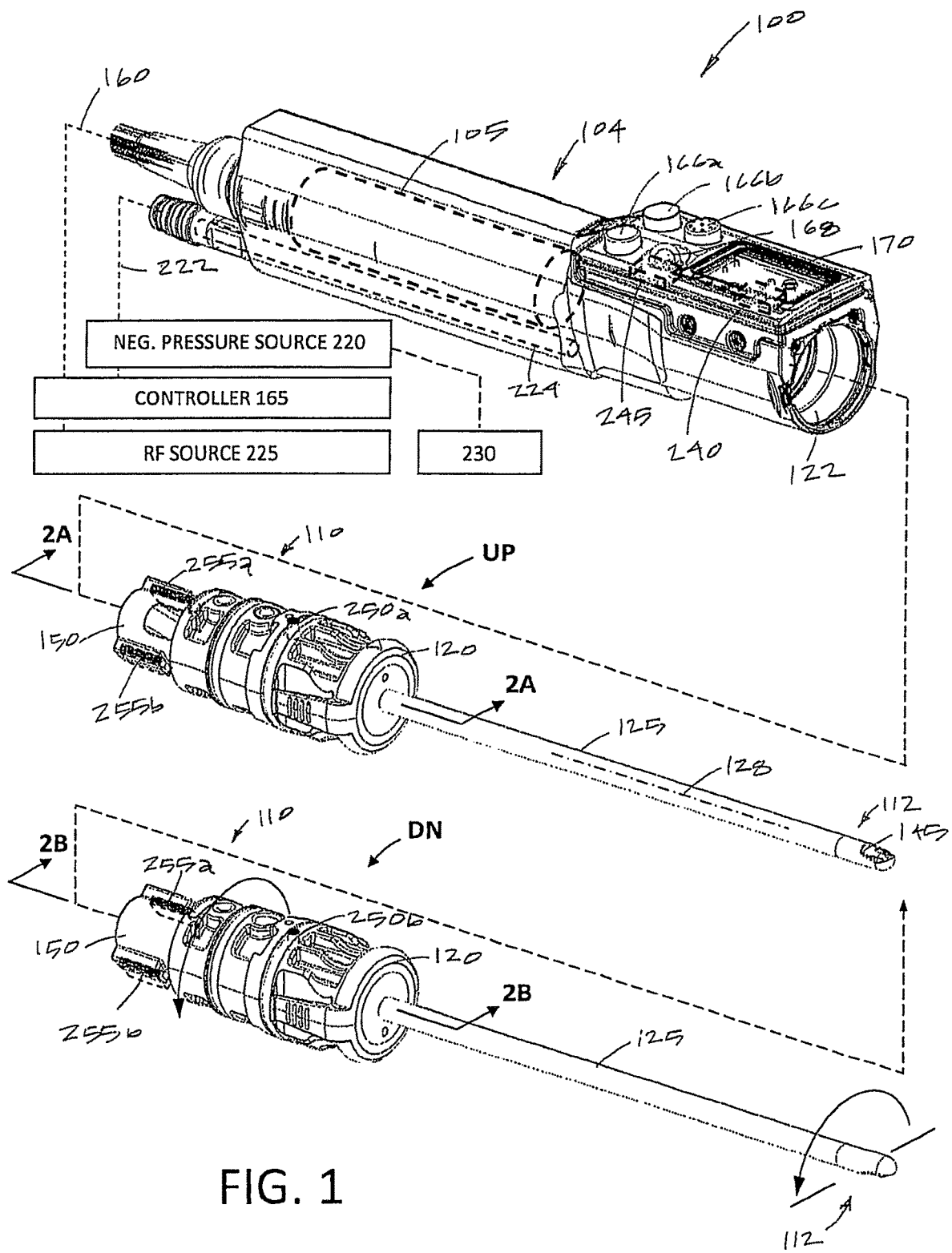
FIG. 1 is a perspective view of an arthroscopic cutting system that includes reusable handpiece with a motor drive and a detachable single-use cutting probe, wherein the cutting probe is shown in two orientations as it may be coupled to the handpiece with the probe and working end in upward orientation or a downward orientation relative to the handpiece, and wherein the handpiece includes an LCD screen for displaying operating parameters of system during use together with control actuators on the handpiece.

In one variation shown in FIG. 1, the arthroscopic system 100 of the present invention provides a handpiece 104 with motor drive 105 and a disposable shaver assembly or probe 110 with a proximal hub 120 that can be received by receiver or bore 122 in the handpiece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
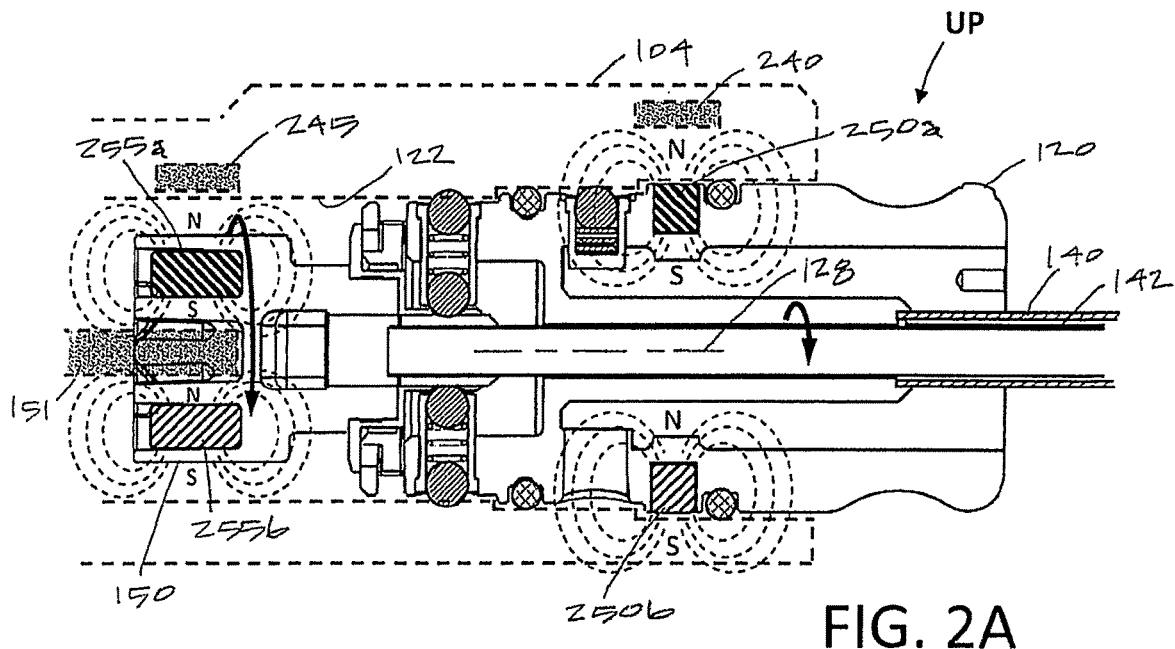
FIG. 2A is an enlarged longitudinal sectional view of the hub of the probe of FIG. 1 taken along line 2A-2A of FIG. 1 with the hub and probe in an upward orientation relative to the handpiece, further showing Hall effect sensors carried by the handpiece and a plurality of magnets carried by the probe hub for device identification, for probe orientation and determining the position of motor driven components of the probe relative to the handpiece.
Figure 3A:
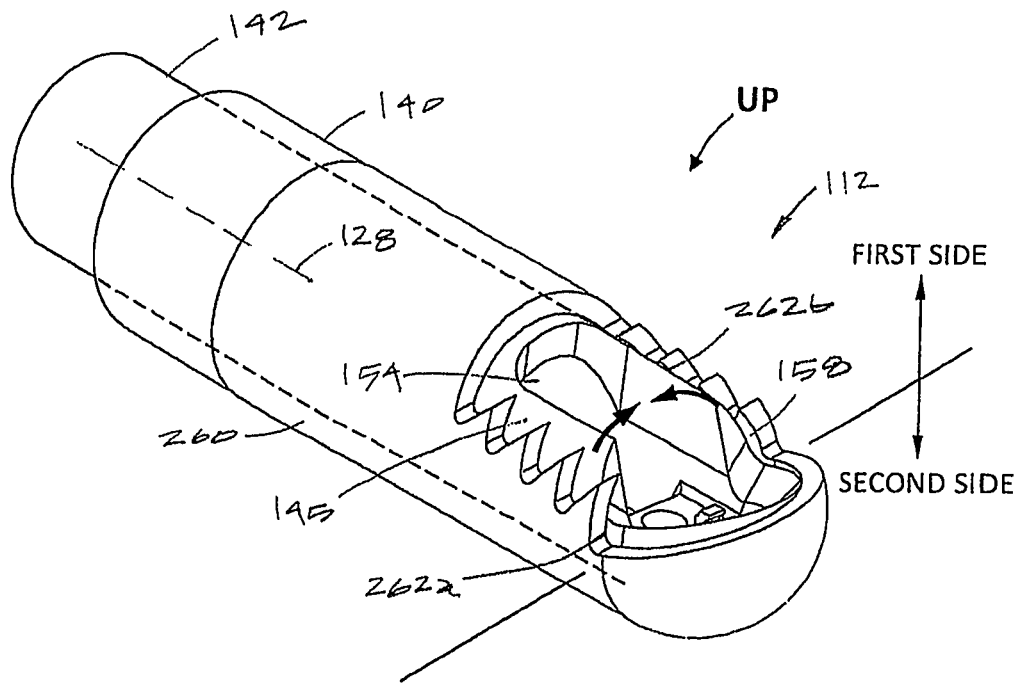
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
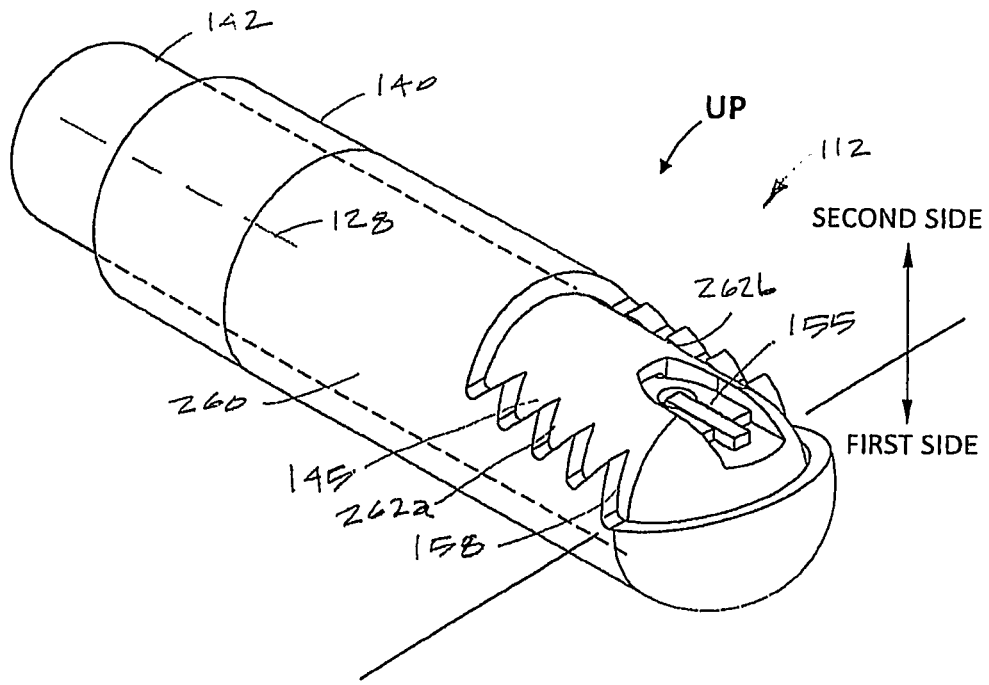
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the handpiece 104. More particularly, the hub 120 can be coupled to the handpiece 104 in an upward orientation indicated at UP and a downward orientation indicated at DN where the orientations are 180° opposed from one another. It can be understood that the upward and downward orientations are necessary to orient the working end 112 either upward or downward relative to the handpiece 104 to allow the physician to interface the cutting member 145 with targeted tissue in all directions without having to manipulate the handpiece in 360° to access tissue.

In FIG. 1, it can be seen that the handle 104 is operatively coupled by electrical cable 160 to a controller 165 which controls the motor drive unit 105 Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the handpiece for displaying operating parameters, such as cutting member RPM, mode of operation, etc.

Figure 4:
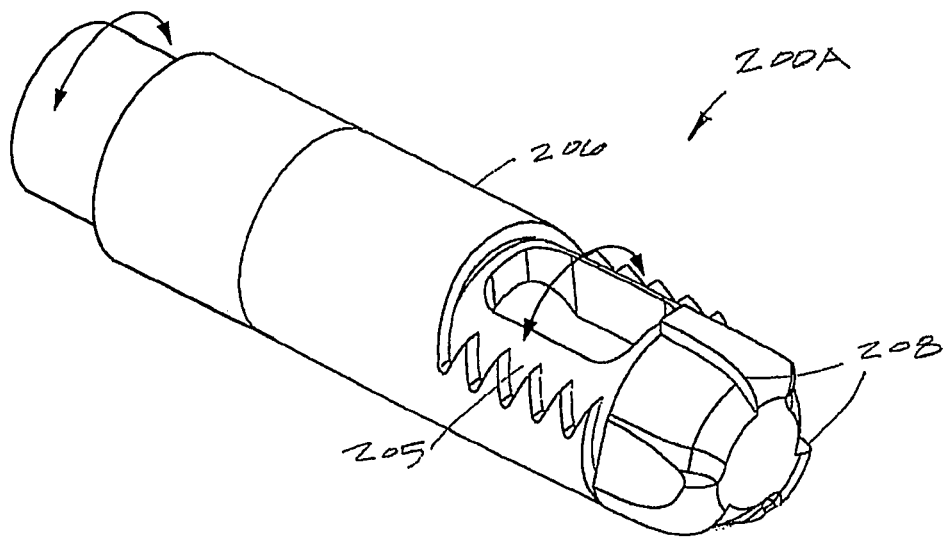
FIG. 4 is a perspective view of a working end of a variation of a probe that may be detachably coupled to the handpiece of FIG. 1, wherein the working end includes a bone burr extending distally from the outer sleeve.
Figure 5:
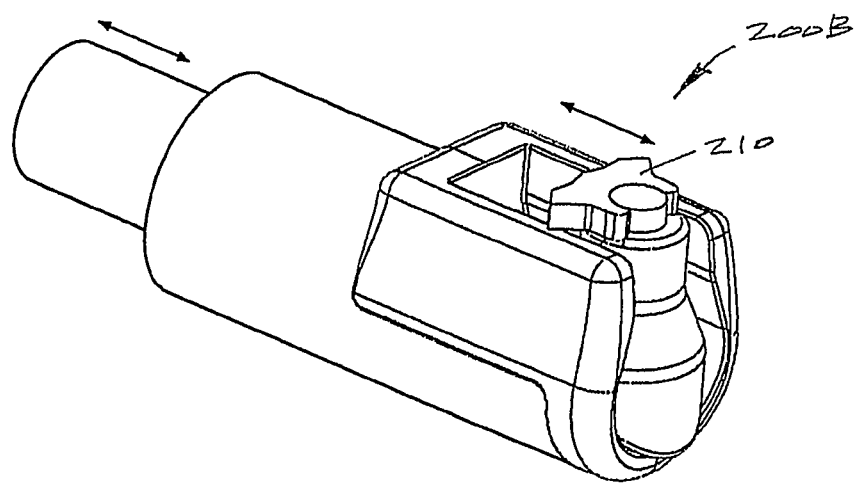
FIG. 5 is a perspective view of a working end of a variation of a probe that may be detachably coupled to the handpiece of FIG. 1, wherein the working end has a reciprocating electrode.
Figure 6:
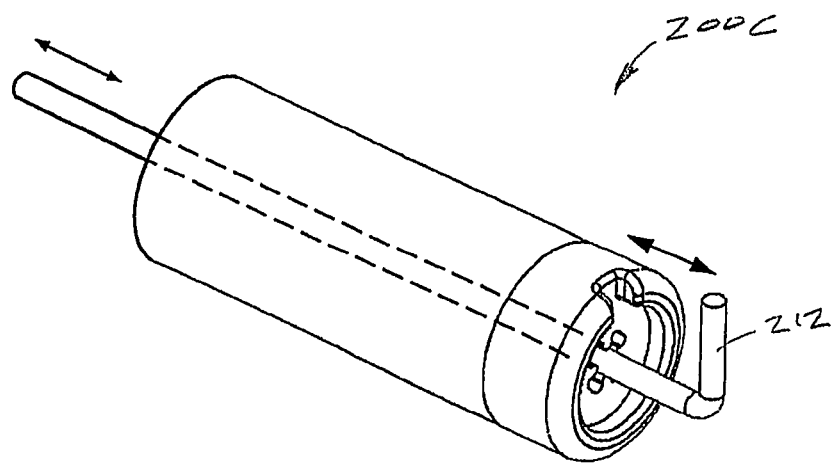
FIG. 6 is a perspective view of a working end of another variation of a probe that may be detachably coupled to the handpiece of FIG. 1, wherein the working end has a hook electrode that has extended and non-extended positions.
Figure 7:
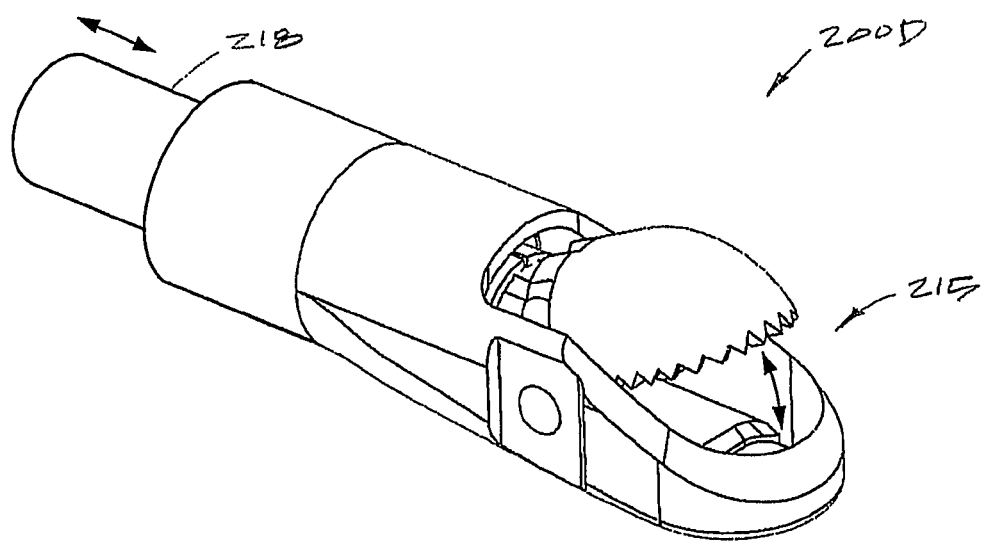
FIG. 7 is a perspective view of a working end of yet another variation of a probe that may be detachably coupled to the handpiece of FIG. 1, wherein the working end has an openable-closeable jaw structure for cutting tissue.

It can be understood from FIG. 1 that the system 100 and handpiece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same handpiece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in handpiece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and handpiece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to handpiece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the handpiece 104 in an upward or downward orientation relative to the handpiece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
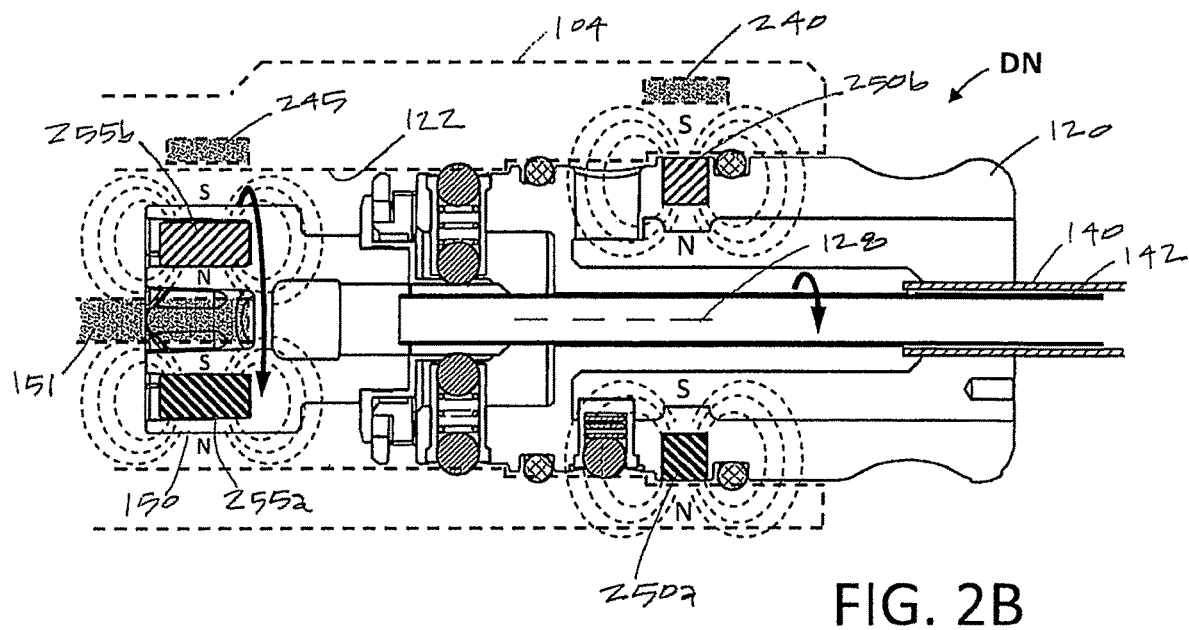
FIG. 2B is a sectional view of the hub of FIG. 1 taken along line 2B-2B of FIG. 1 with the hub and probe in a downward orientation relative to the handpiece showing the Hall effect sensor and magnets having a different orientation compared to that of FIG. 2A.

Referring to FIGS. 1 and 2A-2B, it can be seen that handpiece 104 carries a first Hall effect sensor 240 in a distal region of the handpiece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The handpiece 104 carries a second Hall affect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the handpiece, (ii) the upward or downward orientation of the probe hub 120 relative to the handpiece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in handpiece 104 is in axial alignment with either magnet 250a or 250b when the probe hub 120 is coupled to handpiece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a, 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to handpiece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the handpiece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on handpiece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
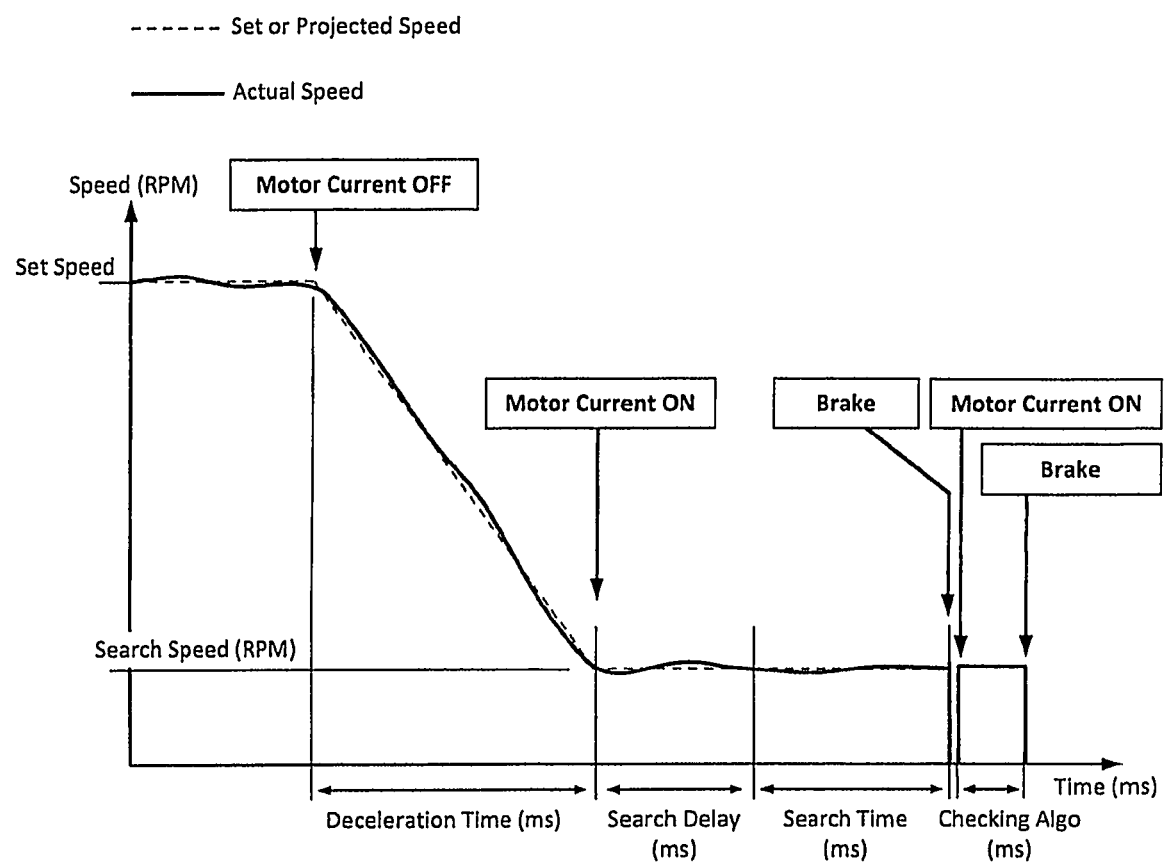
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the handpiece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a handpiece with a motor drive, a controller, and a probe with a proximal hub configured for detachable coupling to the handpiece, wherein the motor drive is configured to couple to a rotating drive coupling in the hub and wherein the drive coupling carries first and second magnets with North and South poles positioned differently relative to said axis, and coupling the hub to the handpiece, activating the motor drive to thereby rotate the drive coupling and magnets at least 180°, using a handpiece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
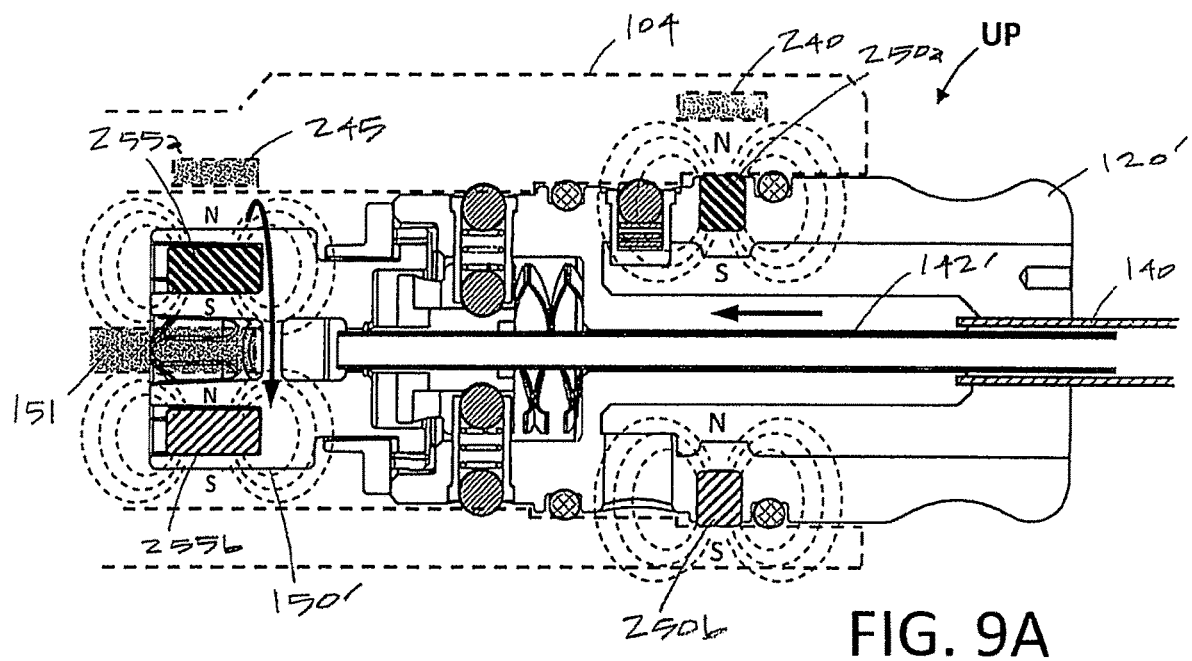
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the handpiece.
Figure 9B:
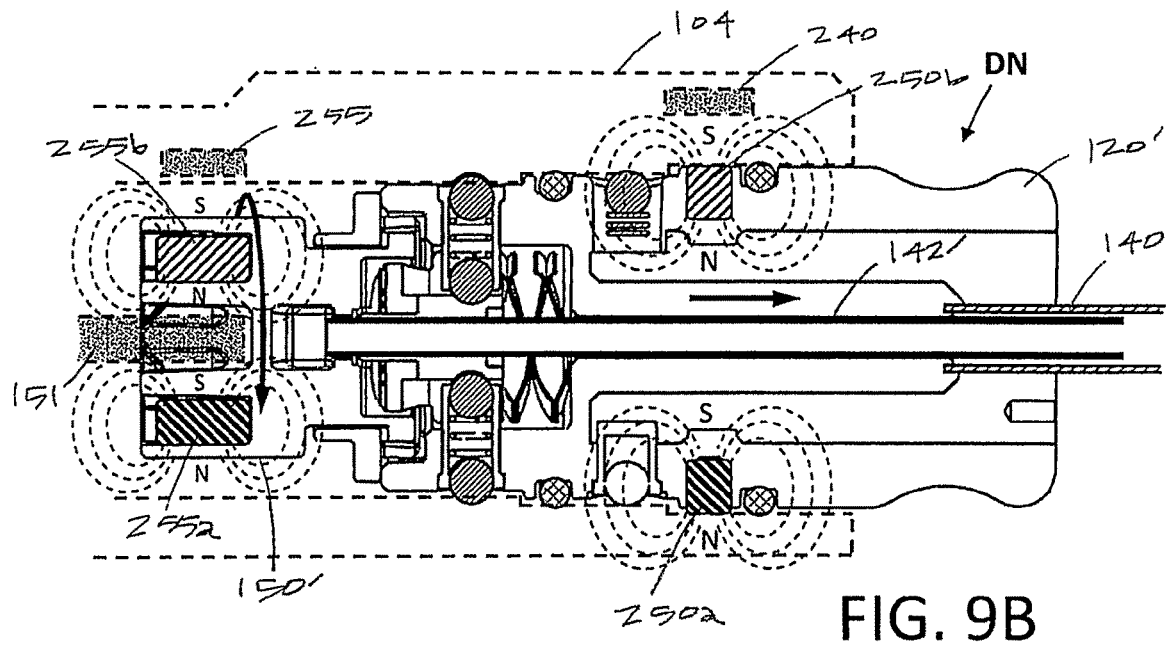
FIG. 9B is a sectional view of the hub of FIG. 9A rotated 180° in a downward facing position relative to the handpiece.

FIGS. 9A-9B are longitudinal sectional views of a probe hub 120' that corresponds to the working end 200B of FIG. 5 which has a reciprocating electrode 210. In FIGS. 9A-9B, the handpiece 104 and Hall affect sensors 240 and 245 are of course the same as described above as there is no change in the handpiece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Now turning to FIGS. 10 and 11A-11C, another variation of an arthroscopic shaver or resection probe 400 is shown which somewhat similar to that of FIGS. 1 and 3A-3B which comprises a tubular cutter having a proximal hub 402 coupled to an elongated shaft assembly 405. The shaft assembly comprises an outer sleeve 410 and a concentric inner sleeve 415 that extends along axis 418 to a working end 420. The hub 402 again is adapted for coupling to a handpiece and motor drive operated by a controller and controller algorithms having the features as described in previous embodiments for rotating the inner sleeve 415 as well as stopping the inner sleeve 415 in a selected rotational position, such as a window-closed or window-open position. The working end 420 again has an outer sleeve window 422 (also referred to as the outer cutting or resection window) that cooperates with an inner sleeve window 425 for engaging and resecting tissue.

The variation in FIGS. 10, 10A and 11A-11C, the shaft assembly 405 differs in that the outer sleeve 410 has a distal end portion that comprises a dielectric body or housing 440 in which the outer window 422 is disposed. In one variation, a proximal 426a and a medial portion 426b of the outer sleeve 410 extend from the hub 402 and comprise a thin-wall, electrically conductive metal tube 428, such as a stainless steel tube. As will be described further below, the proximal and/or medial portions of the metal tube can function as an electrode, for example located at 430 in FIG. 10. In a typical variation, the dielectric housing 440 comprises a ceramic material, a glass material, a polymeric material or a combination thereof. In some variations, the dielectric housing 440 can be carried within a metal support portion 442 which extends distally from the metal outer tube 428 and is positioned underneath or partly surrounding a distal portion of the dielectric housing 440.

Figures 11A, 11B, 11C:
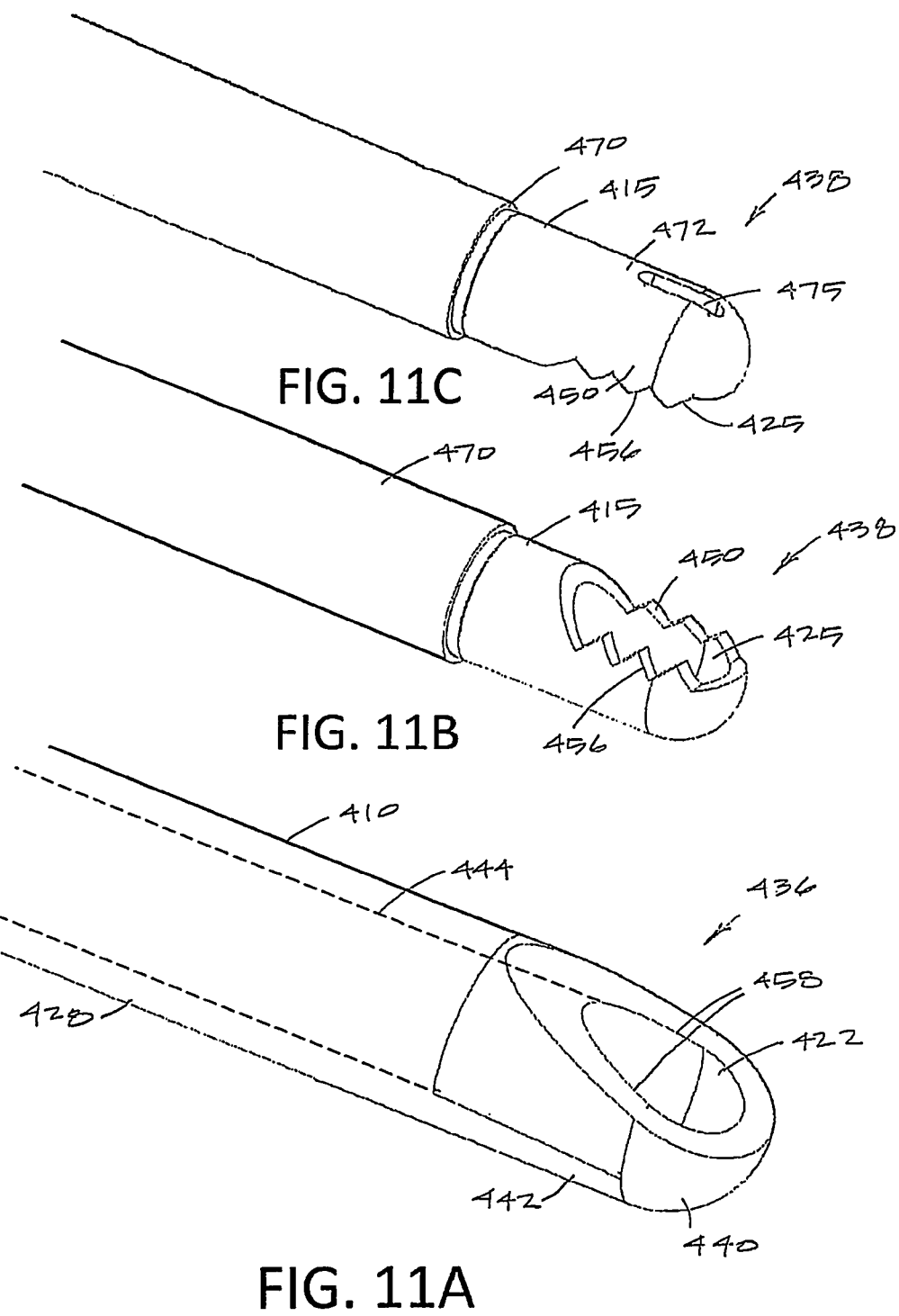
FIG. 11A is perspective view of the working end of the outer sleeve of the probe of FIG. 10 separated from the inner sleeve.
FIG. 11B is perspective view of the working end of the inner sleeve of the probe of FIG. 10 with the inner sleeve window facing upward.
FIG. 11C is perspective view of the working end of the inner sleeve of FIG. 11B with the inner sleeve window facing downward.

FIG. 11A shows a working end 436 of the outer sleeve 410 with the outer cutting or resecting window 422 separated from the inner sleeve 415. It can be seen that an axial passageway or bore 444 extends through the outer sleeve 410 and the dielectric housing 440 in which the concentric inner sleeve 415 (FIGS. 11B and 11C) is co-axially and rotationally disposed.

FIGS. 11B and 11C show a working end 438 of the inner sleeve 415 which extends through the passageway or bore 444 of the outer sleeve 410 of FIG. 11A. The working end 438 is shown in a first position with the inner sleeve window 425 facing upwardly in FIG. 11B. FIG. 11C illustrates the same inner sleeve 415 rotated 180° so that the inner sleeve window 425 is facing downwardly. The inner sleeve 415 comprises a thin-wall tube comprising a metal or other conductive material, such as stainless steel, which can function as an electrode indicated at 450 (FIG. 11C). The electrode 450 of working end 438 of the inner sleeve 415 is typically sized or otherwise configured to have a close rotational fit in the passage way or bore 444 of the dielectric housing 440 so that the inner window edges 456, with optional teeth, and the edges 458 outer sleeve window and act like scissors for shearing or resecting tissue, either mechanically or electrosurgically, as will be described further below. Still referring to FIGS. 11A and 11B, a proximal portion of the inner sleeve 415 is covered by a thin layer 470 of an insulating polymer, such as a heat shrink tubing or a parylene coating, to electrically insulate the outer surface of inner sleeve 415 from the inner surface of the metal outer sleeve 428.

Figure 10A:
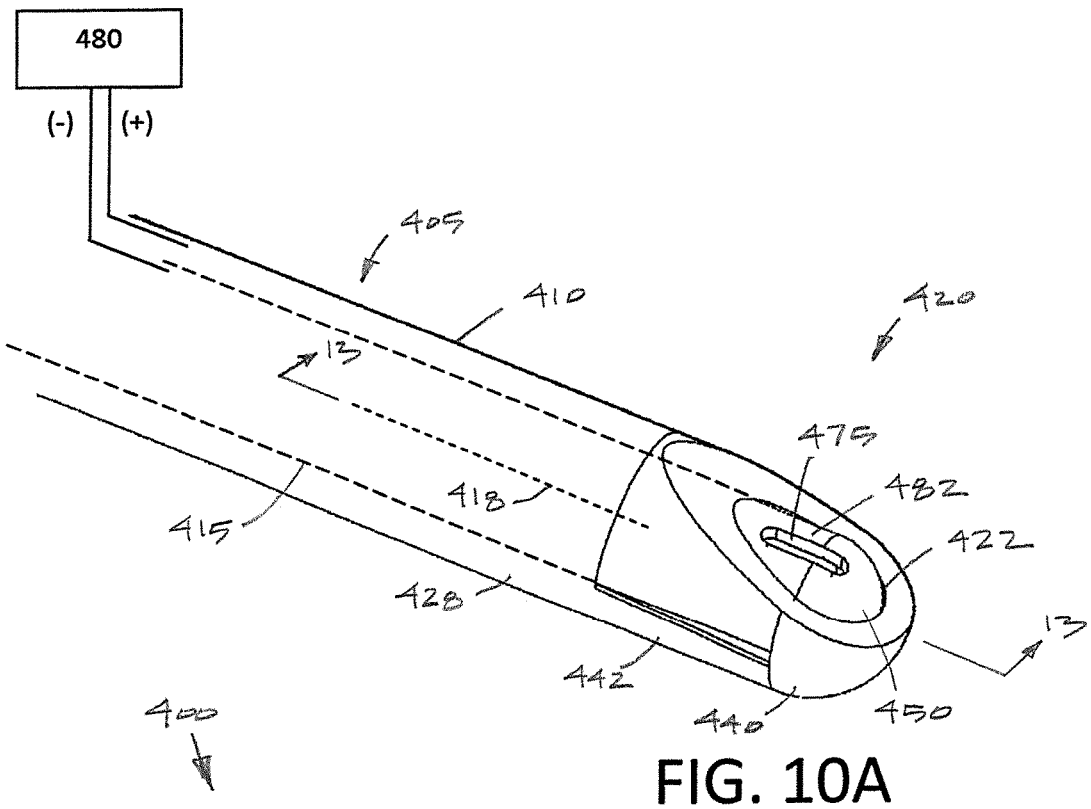
FIG. 10A is an enlarged view of the electrode and outer sleeve carrying a distal dielectric housing of FIG. 10 taken along line 10A-10A.
Figure 10:
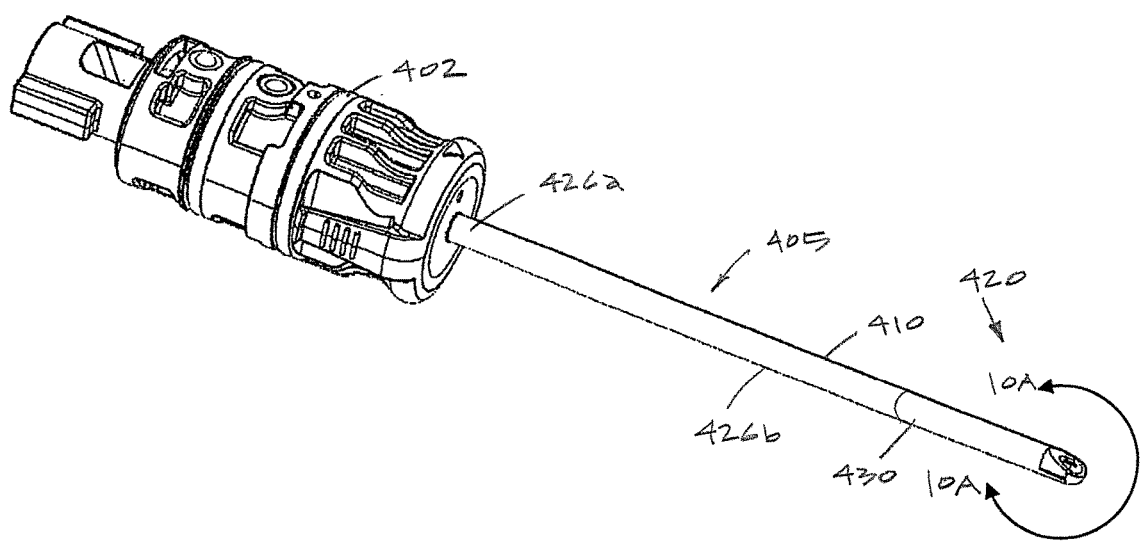
FIG. 10 is a perspective view of another variation of a probe that shows a motor-driven, rotating inner cutting sleeve that comprises an electrode and outer sleeve carrying a distal dielectric housing.

In another aspect of the invention, as can be seen in FIGS. 10 and 11C, the back side 472 of the inner sleeve 415 which opposes the inner sleeve window 425 has at least one opening 475 that is provided for fluid outflows therethrough when the inner sleeve 415 is rotated relative to the outer sleeve 410 to a window-closed position (see FIG. 1).

Figure 12:
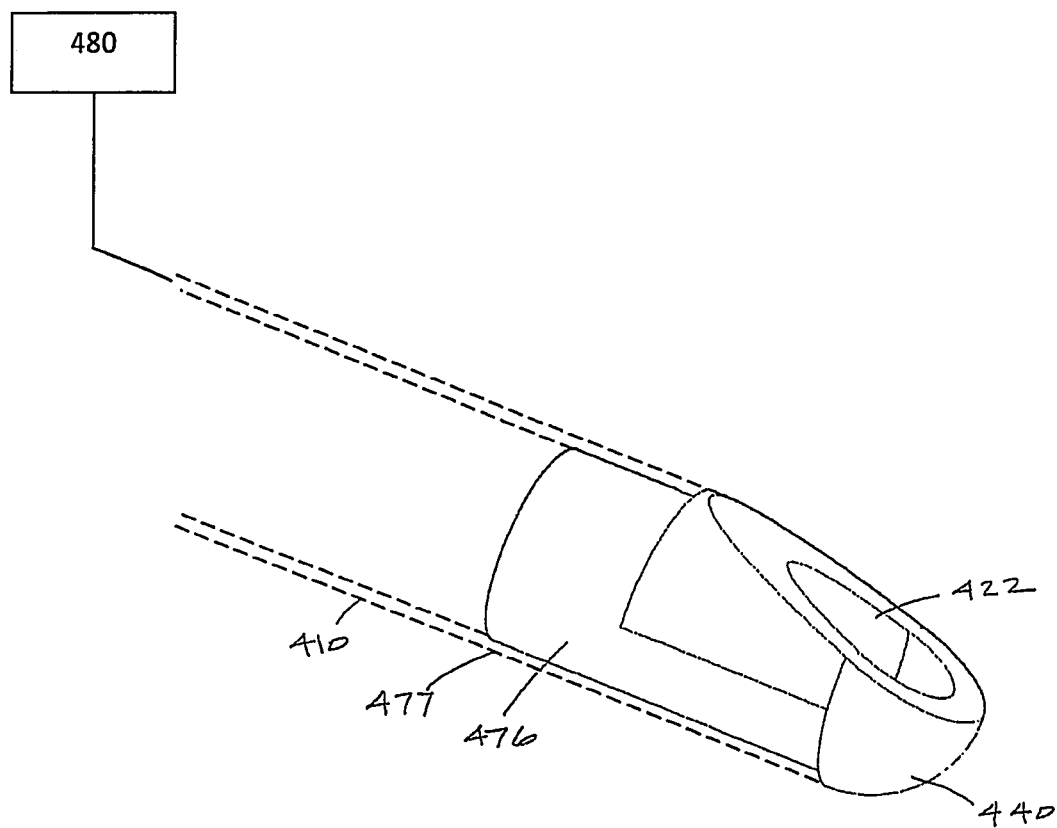
FIG. 12 is perspective view of the dielectric housing of FIG. 11A.

FIG. 12 illustrates the dielectric or ceramic housing or portion 440 with the outer sleeve 410 shown in phantom view. It can be seen that the dielectric housing 440 has a recessed portion 476 in which a distal end or extension 477 of outer sleeve 410 surrounds and supports the dielectric housing 440. The thickness of a wall of the dielectric housing around the window 422 can range from about 0.05" to 0.20".

Figure 13:
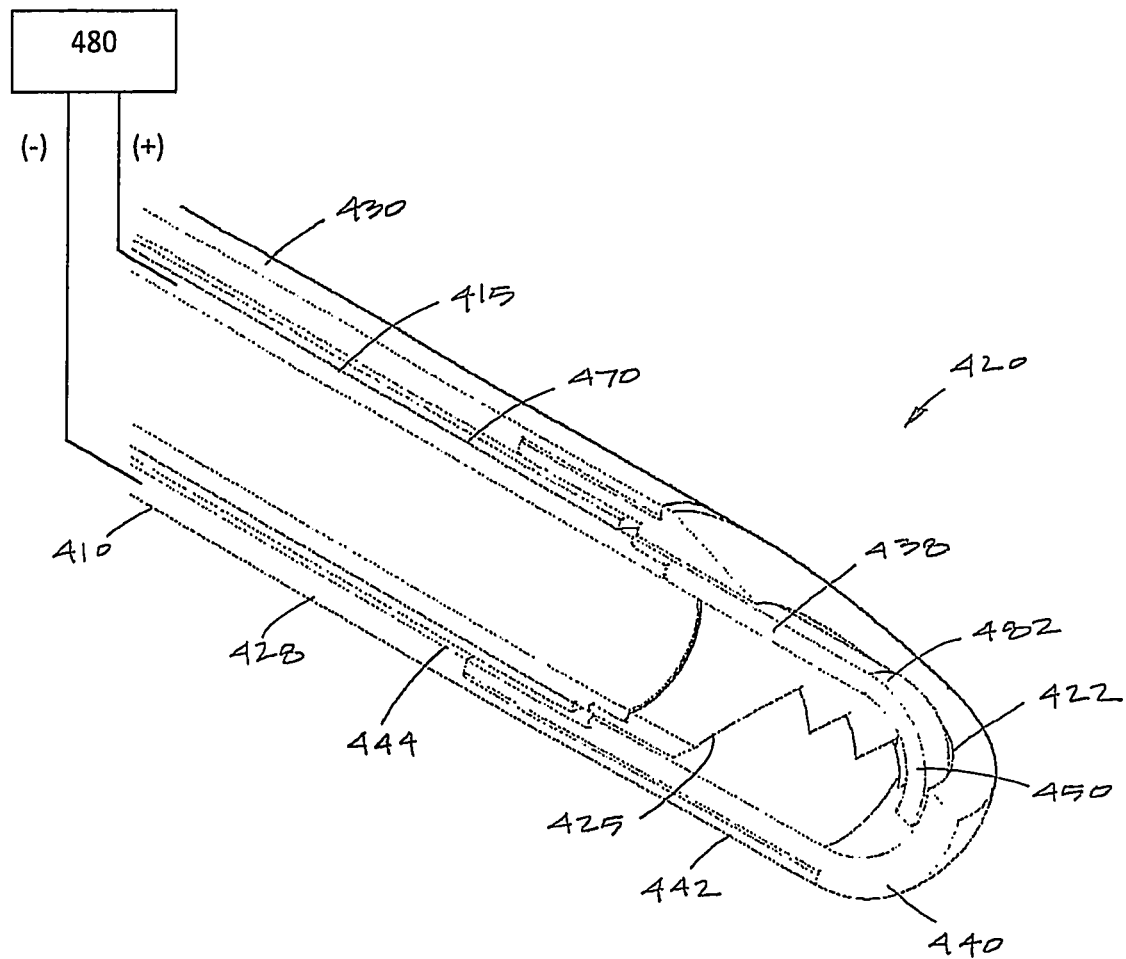
FIG. 13 is a sectional view of the working end of FIG. 10 taken along line 13-13 of FIG. 10.

FIG. 13 is a longitudinal sectional view of the working end 420 of the probe of FIGS. 10-11C which shows the working end 420 in its window-closed position. It can be seen that the working end 438 of the inner sleeve 415 is in close tolerance with bore 444 in the dielectric housing 440 so that rotation of inner sleeve 415 can shear tissue protruding through the inner sleeve and outer sleeve windows 422, 425. FIG. 13 further illustrates how the support portion 442 of the metal outer sleeve 428 extends underneath the ceramic housing or portion 440. In addition, FIG. 13 also shows the thin insulating layer 470 that surrounds the inner sleeve 415 to electrically insulate the inner sleeve from the metal outer sleeve 428.

Still referring to FIG. 13, an RF source 480 is coupled to both the inner sleeve 410 and the outer sleeve 415 to provide for electrosurgical functionality. The RF source 480 is capable of delivering an average of at least 100W, often at least 200W, more often at least 300W and frequently at least 400W to allow for ignition of a plasma over the exposed outward or exterior surface 482 of the inner sleeve 415 in the window-closed position as shown in FIG. 10. Typically, the outward surface 482 of the inner sleeve 415 in the window-closed position has an area less than 15 mm$^2$, often less than 10 mm$^2$, and frequently less than 8 mm$^2$. Rotation of the inner sleeve 415 in the outer sleeve 410 in a first mode of operation can mechanically shear tissue protruding through the windows 422 and 425 while operation in a second mode can electrosurgically resect such tissue. That is, the inner sleeve can rotate and shear tissue while the RF source 480 contemporaneously delivers the cutting current to the inner sleeve to energize the edges of the inner sleeve window 425 which can create a plasma to shear tissue or to assist in shearing tissue.

In general, a resecting probe or treatment device corresponding to the invention comprises shaft assembly 405 having an outer sleeve 410 and a rotatable inner sleeve 415 co-axially received in a bore 444 in outer sleeve, wherein the inner and outer sleeves have respective inner and outer cutting or "resecting" windows, 422 and 425, with cooperating cutting edges in distal portions thereof, and wherein the distal portion of the outer sleeve that carries the cutting window 422 comprises a dielectric housing 440 and the distal working end 438 of the inner sleeve 415 that carries an inner cutting or resecting window 425 and comprises an RF electrode 450.

In this variation, the dielectric material of the dielectric housing can comprises at least one of a ceramic, a glass and a polymer. For example, the ceramic material can be selected from the group consisting of alumina, zirconia, silicon nitride, yttria-stabilized zirconia, magnesia-stabilized zirconia, ceria-stabilized zirconia and zirconia toughened alumina.

The probe of FIG. 10 further comprises a motor configured to selectively rotate in the inner sleeve in first and second rotational directions, with the radiofrequency (RF) source 480 coupled to the electrode. Further, a controller is operatively coupled to the motor and to the RF source.

In general, the controller includes an algorithm for stopping the motor to position the inner sleeve in a window-closed position or a window-open position. Further, the controller is configured to selectively operate in (i) a first mode in which the motor rotates or oscillates the inner sleeve with the RF electrode not energized for mechanically cutting tissue; (ii) a second mode in which the motor rotates or oscillates the inner sleeve with the RF electrode energized for electrosurgically cutting tissue; (iii) a third mode in which the inner sleeve is stationary in the window-closed position and the RF electrode is energized for applying coagulative or ablative energy to tissue; and (iv) a fourth mode in which the inner sleeve is stationary in the window-open position and the RF electrode is energized for applying coagulative or ablative energy to tissue.

Figure 14:
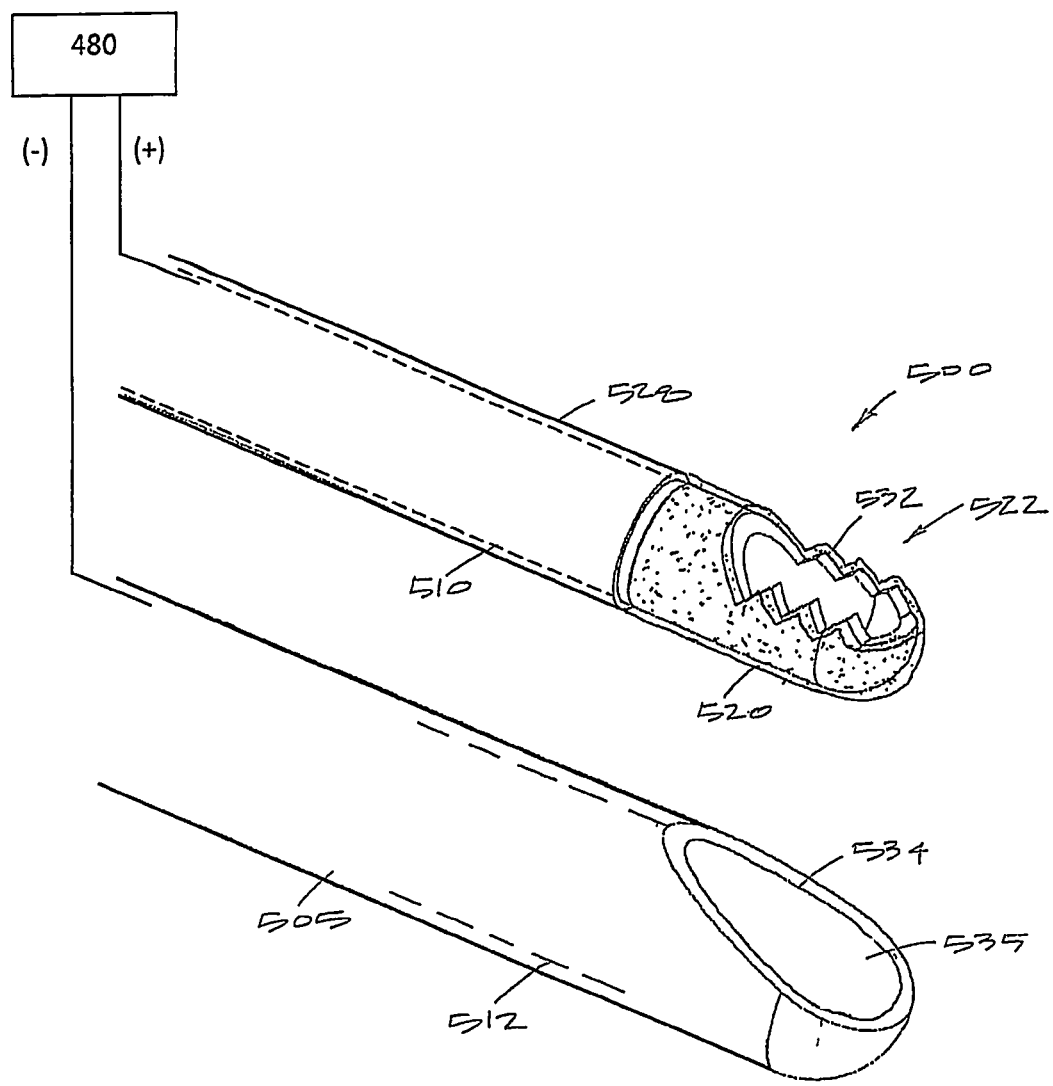
FIG. 14 illustrates an alternative working end.

FIG. 14 illustrates another variation of a working end 500 that includes an outer sleeve 505 and inner sleeve 510 that is adapted to rotate in bore 512 of the outer sleeve. In this variation, the outer sleeve 505 comprises a conductive metal tube without the ceramic housing or portion as in the previous variation of FIGS. 10 and 11A. In this variation, the dielectric component that separates the conductive inner sleeve 510 from the conductive outer sleeve comprises a dielectric coating or layer 520 on the distal end 522 of the inner sleeve 510 and the polymer coating 528 over the proximal and medial portions of the inner sleeve 510. The dielectric material 520 at the distal end 522 of the inner sleeve can be a ceramic or a glass material that can be configured with sharp edges 532 so as to provide a sharp, durable cutting edges 532 for cooperating with the edges 534 of the outer sleeve window 535. In all other respects, the variation of FIG. 14 can operate is the same manner as the variation described above in FIGS. 10-13.

Figure 15:
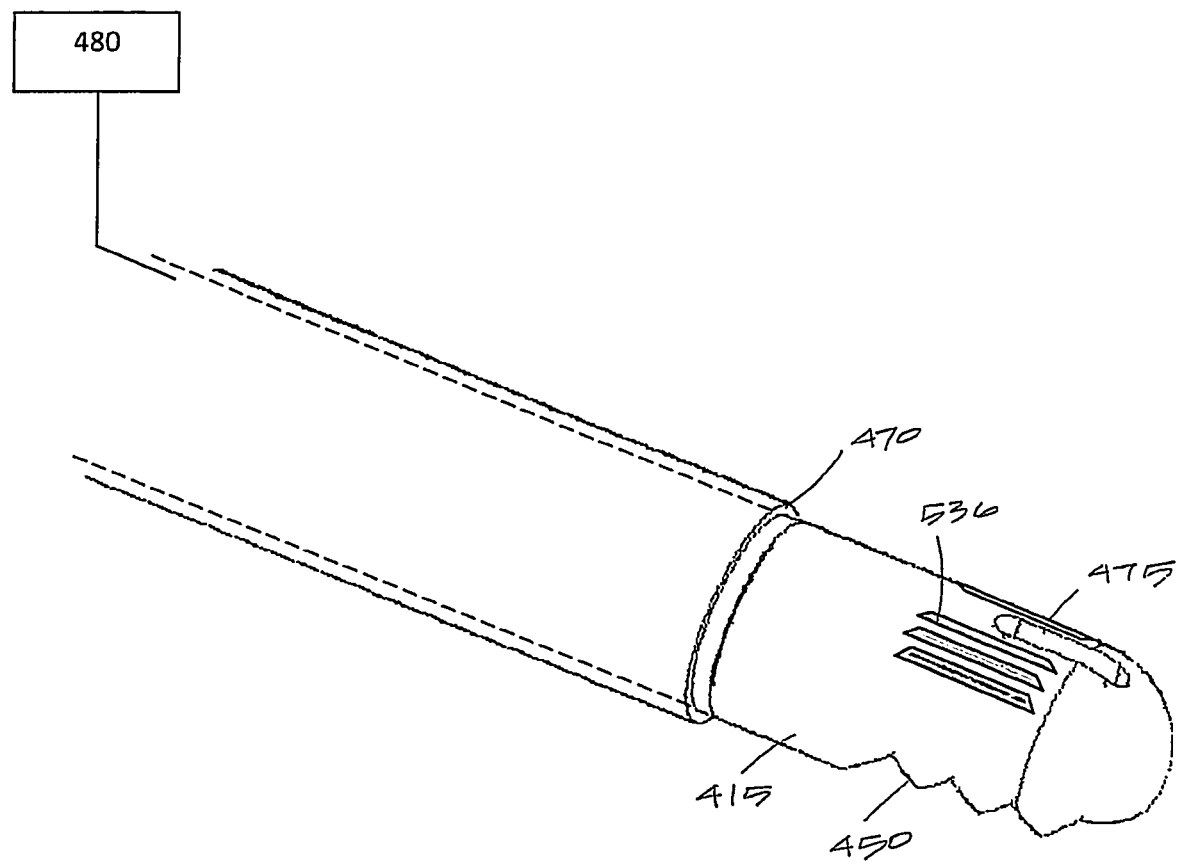
FIG. 15 is a perspective view of a working end of a motor-driven, rotating inner sleeve similar to that of FIGS. 11B-11C with abrasive cutting features for abrading bone.

FIG. 15 is a perspective view of a working end of a motor-driven, rotating inner sleeve similar to that of FIGS. 11B-11C with abrasive cutting features or sharp edges 536 for abrading bone. Thus, another mode of operation can be to rotate the inner sleeve at high speeds to use the abrasive features 536 to cut or abrade bone, typically without RF current being applied to the electrode surface. In some methods, and RF current can be applied to the electrode surface while abrading hard tissue or cauterizing purposes.

Figure 16:
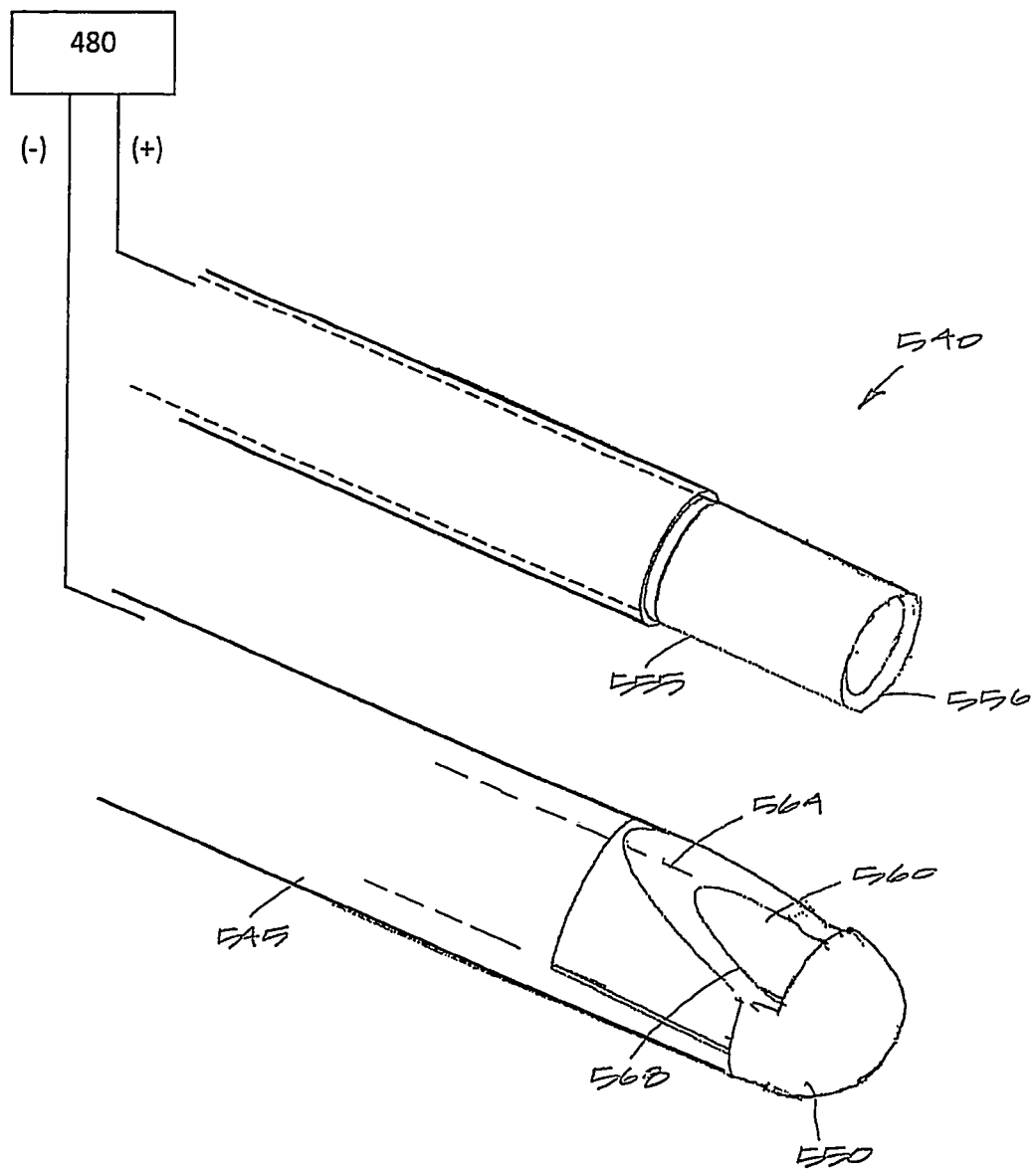
FIG. 16 is a perspective view of a working end of another variation of a probe that shows a motor-driven, reciprocating inner sleeve comprising an electrode that reciprocates in a dielectric housing carried by the outer sleeve.

FIG. 16 illustrates another variation of working end 540 that operates under similar principles to that of the variation of FIG. 10 wherein the outer sleeve 545 carries a distal dielectric or ceramic housing or portion 550 and a concentric inner sleeve 555 with cutting edges 556 is adapted to move relative to the outer sleeve window 560 in the dielectric housing 550. However, in this variation, the inner sleeve 555 is adapted to reciprocate rather than rotate. In other respects, the cutting edges 556 of the inner sleeve 555 are configured with a close fit to the bore 564 in the dielectric housing 550 such that the inner sleeve cutting edges 556 and the edges 568 of outer sleeve window 560 shear tissue engaged by the window 560. As described in previous embodiments, an RF source 480 is operatively coupled to both the inner and outer sleeves 545 and 555 to allow for electrosurgical cutting. In use, the reciprocation of inner sleeve thus can resect tissue mechanically or electrosurgically as described above.

Figure 17:
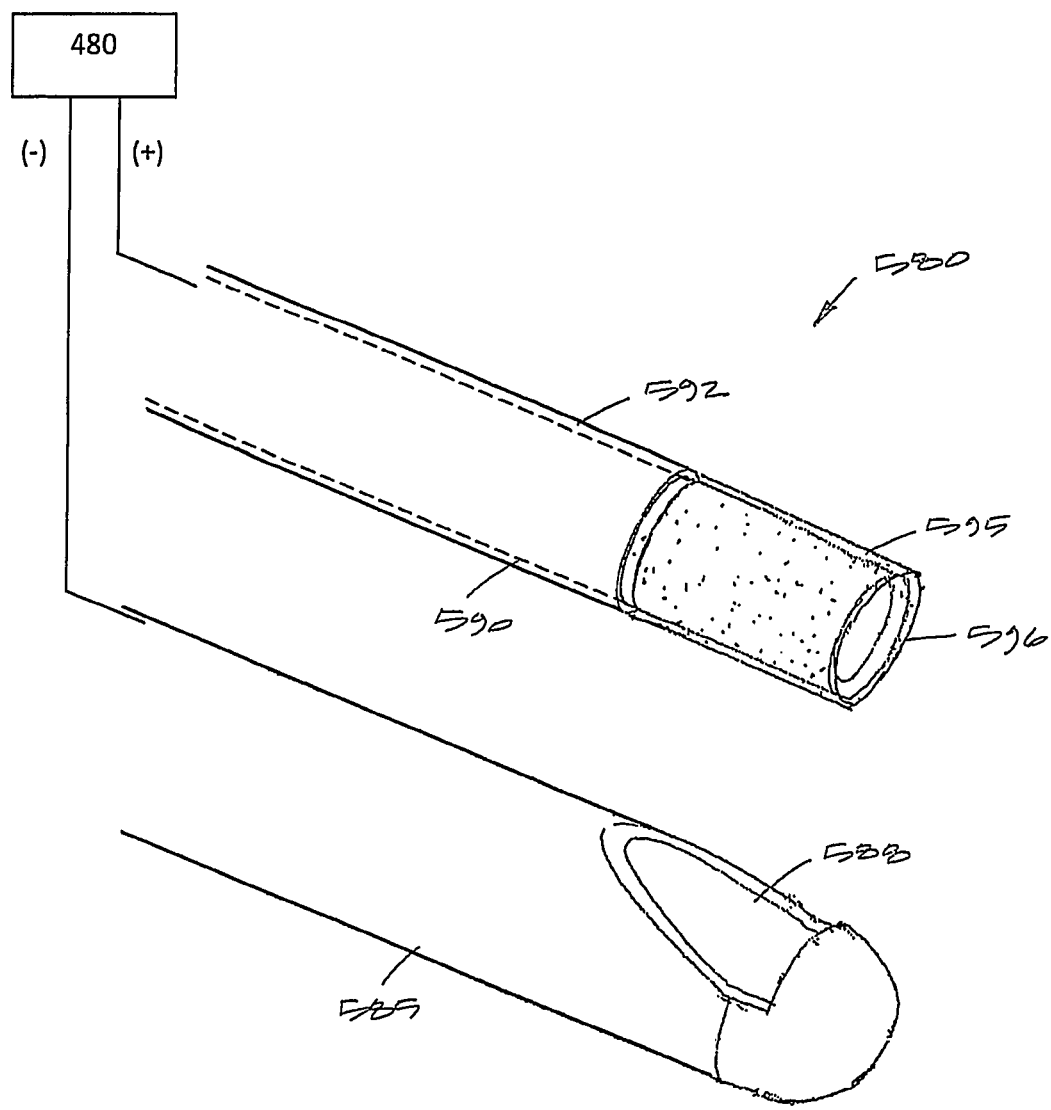
FIG. 17 is a perspective view of a working end of another variation of a probe that shows a reciprocating inner sleeve with a ceramic or glass cutting edge surrounding an electrode sleeve that reciprocates in a metal outer sleeve.

FIG. 17 illustrates another variation of working end 580 that again is similar to that of FIGS. 14 and 15. In this variation, the outer sleeve 585 comprises a thin wall conductive metal with window 588 therein. The inner sleeve 590 comprises a metal sleeve encased in an insulative polymer 592 and a distal ceramic or glass portion 595 that functions as an electrical insulator as well as providing a cutting edge 596. In this variation, the inner sleeve 590 again is adapted to reciprocate rather than rotate in the outer sleeve window 588. Again, an RF source 480 is operatively coupled to both the inner and outer sleeves 585 and 590 to allow for electrosurgical cutting. In use, the reciprocation of inner sleeve and thus can resect tissue mechanically or electrosurgically as described above.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A tissue treatment device, comprising:
   a shaft assembly including an outer sleeve and an inner sleeve, the inner sleeve co-axially and rotatably received in an axial passageway of the outer sleeve and including an inner cutting window formed therein, the outer sleeve comprising a metal tube;

a dielectric housing forming a distal portion of the outer sleeve and including an outer cutting window formed in a distal section of the dielectric housing, the dielectric housing including a proximal section that is received in a distal portion of the metal tube such that the distal section of the dielectric housing is left extending distally of the distal portion of the metal tube, the distal portion of the metal tube fully surrounding the proximal section of the dielectric housing, the metal tube including a metal extension portion that extends distally of the distal portion of the metal tube alongside a lower outer surface of the distal section of the dielectric housing, the metal extension portion only partially surrounding the distal section of the dielectric housing so as to leave the outer cutting window exposed in the distal portion of the outer sleeve;

a radiofrequency (RF) electrode formed by a distal portion of the inner sleeve, wherein said outer cutting window and said inner cutting window include respective sharp outer window cutting edges and sharp inner window cutting edges, said sharp outer window cutting edges formed by a dielectric material of the dielectric housing, wherein the lower outer surface of the distal section of the dielectric housing provides a recessed area into which the metal extension portion is received for supporting the distal section of the dielectric housing, the recessed area being recessed relative to an upper outer surface of the distal section of the dielectric housing that surrounds the outer cutting window.

2. The tissue treatment device of claim 1, wherein the dielectric housing comprises at least one of a ceramic, a glass or a polymer.

3. The tissue treatment device of claim 1, wherein the dielectric housing comprises a ceramic selected from the group consisting of alumina, zirconia, silicon nitride, yttria-stabilized zirconia, magnesia-stabilized zirconia, ceria-stabilized zirconia and zirconia toughened alumina.

4. The tissue treatment device of claim 1 further comprising:
a motor configured to selectively rotate the inner sleeve in first and second rotational directions; and
a radiofrequency (RF) source configured to couple to the RF electrode.

5. The tissue treatment device of claim 4 further comprising a controller operatively coupled to the motor and to the RF source.

6. The tissue treatment device of claim 5, wherein the inner sleeve can be rotated to at least a window-closed position where the inner cutting window is covered by a wall of the dielectric housing and to a window-open position where the inner cutting window is aligned with the outer cutting window in the dielectric housing, and wherein the controller is configured to stop the motor to position the inner sleeve in at least the window-open and the window-closed positions.

7. The tissue treatment device of claim 6, wherein the controller is configured to selectively operate the motor and the RF source in at least a first mode, a second mode; a third mode, and a fourth mode, wherein (1) the controller is configured to operate the motor to rotate or oscillate the inner sleeve without energizing the RE source for mechanically cutting the tissue in the first mode, (2) the controller is configured to operate the motor to rotate or oscillate the inner sleeve and energizes the RF source for electrosurgically cutting the tissue in the second mode, (3) the controller is configured to energize the RF source while the inner sleeve is stationary in the window-closed position to apply coagulative or ablative energy to the tissue through the RF electrode in the third mode; and (4) the controller is configured to energize the RF source while the inner sleeve is stationary in the window-open position to apply the coagulative or ablative energy to the tissue the fourth mode.

8. The tissue treatment device of claim 6 further comprising an opening in a surface of the inner sleeve opposing the inner cutting window for allowing fluid outflow therethrough when the inner sleeve is in the window-closed position.

9. The tissue treatment device of claim 1, wherein the metal extension portion being received in the recessed area creates a continuous outer surface along the outer sleeve between the metal extension portion and portions of the lower outer surface of the distal section of the dielectric housing surrounding the recessed area.

10. The tissue treatment device of claim 1, wherein the proximal section of the dielectric housing includes an outer surface that is recessed relative to an upper outer surface of the distal section of the dielectric housing that surrounds the outer cutting window.

11. The tissue treatment device of claim 1, wherein the metal extension portion extends to the outer cutting window.

12. The tissue treatment device of claim 1, wherein the outer cutting window includes a proximal end, the metal extension portion extending distally of the proximal end of the outer cutting window in a longitudinal direction along the outer sleeve.

13. The tissue treatment device of claim 1, wherein the inner cutting window is formed in a metal wall of the inner sleeve so that the sharp inner window cutting edges are formed by a metal material of the inner sleeve.

14. The tissue treatment device of claim 13, wherein the sharp inner window cutting edges form part of the RF electrode which functions as a first electrode in the tissue treatment device, the metal tube of the outer sleeve functioning as a second electrode in tissue treatment device.

* * * * *